(12) United States Patent
Collins et al.

(10) Patent No.: US 6,320,061 B1
(45) Date of Patent: Nov. 20, 2001

(54) SOLVENT EXCHANGE PROCESS

(75) Inventors: Nick Allen Collins, Fall Branch; Steven Thomas Perri, Kingsport, both of TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 09/587,752

(22) Filed: Jun. 5, 2000

(51) Int. Cl.$^7$ .................................................. C07D 307/62
(52) U.S. Cl. ............................................................ 549/315
(58) Field of Search ............................................ 549/315

(56) References Cited

U.S. PATENT DOCUMENTS

| | | | |
|---|---|---|---|
| 2,421,611 | 6/1947 | Gray ........................ | 195/47 |
| 2,421,612 | 6/1947 | Gray ........................ | 195/47 |
| 2,462,251 | 2/1949 | Bassford, Jr. et al. ............... | 549/315 |
| 4,113,771 | 9/1978 | Lawrence, Jr. et al. ............. | 562/568 |
| 4,191,841 | 3/1980 | Soreau et al. ........................ | 562/475 |
| 4,202,828 | 5/1980 | Matsuura et al. .................... | 562/408 |
| 4,334,074 | 6/1982 | Peterson ................................ | 546/327 |
| 4,699,999 | 10/1987 | El-Chahawi et al. ................ | 562/450 |
| 4,771,001 | 9/1988 | Bailey et al. ......................... | 435/139 |
| 4,990,441 | 2/1991 | Barthole et al. ..................... | 435/138 |
| 5,128,487 | 7/1992 | Tomislav et al. .................... | 549/315 |
| 5,159,110 | 10/1992 | Thunberg ............................. | 562/554 |
| 5,168,055 | 12/1992 | Datta et al. .......................... | 435/145 |
| 5,202,475 | 4/1993 | Cook et al. .......................... | 562/509 |
| 5,202,476 | 4/1993 | Tsuda et al. ......................... | 562/513 |
| 5,210,296 | 5/1993 | Cockrem et al. .................... | 562/589 |
| 5,349,074 | 9/1994 | Bonaldi ................................ | 552/551 |
| 5,391,770 | 2/1995 | Le Fur et al. ........................ | 549/315 |
| 5,410,076 | 4/1995 | Coope et al. ........................ | 562/450 |
| 5,426,219 | 6/1995 | Lehnhardt et al. .................. | 562/580 |
| 5,449,824 | 9/1995 | Felman et al. ....................... | 562/580 |
| 5,522,995 | 6/1996 | Cockrem .............................. | 210/637 |
| 5,712,131 | 1/1998 | Felman et al. ....................... | 435/136 |
| 5,741,681 | 4/1998 | Kato et al. ........................... | 435/109 |
| 5,827,700 | 10/1998 | Felman et al. ....................... | 435/144 |
| 5,852,211 | 12/1998 | Dümpelmann et al. ............. | 562/580 |

FOREIGN PATENT DOCUMENTS

922949 * 6/1947 (FR) .

OTHER PUBLICATIONS

Chemical Abstracts, vol. 82, 65021 [Zh. Prikl. Khim, (Leningrad), 47(11), p. 2530–2532 (1974)], 1975.*

Anderson, et al., "Production of 2–Keto–L–Gulonate, an Intermediate in l–Ascorbate Synthesis, by a Genetically Modified *Erwinia herbicola*," Science, vol. 230, pp. 144–149 (1985).

Reichstein, et al., "Eine Ergiebige Synthesis der L–Ascorbinsäure (C–Vitamin)$^2$)," Helv. Chim. Acta, vol. 17:311–328 (1934).

Saito, et al., "Cloning of Genes for L–Sorbose and L–Sorbosone Dehydrogenases from *Gluconobacter oxydans* and Microbial Production of 2–Keto–L–Gulonate, A Precursor of L–Ascorbic Acid, in a Recombinant *G. oxydans* Strain," Applied & Environmental Microbiol., 63(2):454–460 (1997).

* cited by examiner

*Primary Examiner*—Bernard Dentz
(74) *Attorney, Agent, or Firm*—Cheryl J. Tubach; Bernard J. Graves, Jr.

(57) ABSTRACT

A process for recovering an organic acid or a metal salt thereof includes contacting an alcoholic phase containing one or more organic acid(s) or metal salt(s) thereof with water under conditions effective to provide an aqueous phase containing a portion of the organic acid(s) or metal salt(s) thereof. The aqueous phase does not contain substantial amounts of the alcohol(s). This process can also include recovery of the organic acid(s) or metal salt(s) thereof from the aqueous phase.

38 Claims, 4 Drawing Sheets

SOLVENT EXCHANGE PROCESS

ACKNOWLEDGMENT

This invention was made with United States Government support under Cooperative Research Agreement No. 70NANB5H1138 awarded by the Advanced Technology Program of the National Institute of Standards and Technology. The United States Government has certain rights in the invention.

BACKGROUND OF THE INVENTION

1. Field of the Invention

The present invention relates to a solvent exchange process, and in one embodiment, a process that is capable of separating an organic acid such as ascorbic acid from an alcoholic phase.

2. Background Art

Attempts to efficiently and effectively separate an organic acid from an alcoholic phase in which the acid resides have proven to be quite inefficient. In particular, one environment which these inefficiencies have been particularly apparent relates to the production of ascorbic acid.

L-ascorbic acid (vitamin C) has been produced commercially by way of chemical fermentation processes starting from glucose or sorbose. A common intermediate generated during the fermation process is 2-keto-L-gulonic acid or its protected form of diacetone-2-keto-L-gulonic acid. In the case of 2-keto-L-gulonic acid, a process involves esterification of the sugar with methanol followed by cyclization using stoichiometric amounts of base. This process has evolved from the original Reichstein process (T. Reichstein, A. Grussner, *Helv. Chim. Acta* 17, p. 311, 1934).

Recent modifications to the Reichstein process have become more prevalent as alternative fermentation processes for producing 2-keto-L-gulonic acid directly from glucose or sorbose have been reported. These processes have eliminated or removed some of the chemical processing steps prior to production of 2-keto-L-gulonic acid in the Reichstein process. However, these processes have necessitated the separation and purification of ascorbic acid from its alcoholic or aqueous alcoholic solution, all initiated from an alkali metal ascorbate.

Figure 1:
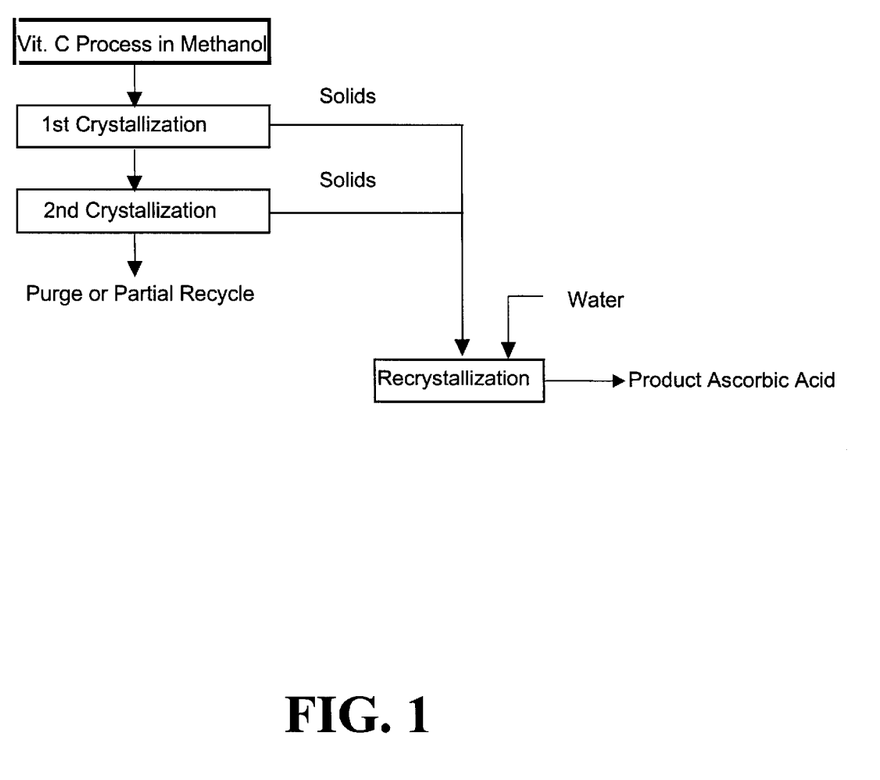
FIG. 1 illustrates a prior art system for removing an acid from an alcoholic phase.

The esterification and cyclization processes employed in the art utilized an organic solvent with the cyclization step and therefore eventually include an isolation of either solid alkali ascorbate or solid ascorbic acid by dissolving the solid in water with subsequent crystallization from water. A typical arrangement is illustrated by FIG. 1 in which the feed involves ascorbic acid in an alcoholic phase. The solids are removed by a series of crystallization steps and then dissolved in, and recrystallized from, water to provide the desired final product.

As can be seen, this series of processing steps necessitates a complex separation system. Solid-liquid handling equipment such as crystallizers are needed for switching from the organic solvent to an aqueous-based solvent system as well as similar solid-liquid handling equipment as required from isolating purified ascorbic acid from water. Such complexities greatly add to the cost of the overall process.

Thus, the need still exist for a method of more efficiently removing acids, and in particular, ascorbic acid, from alcoholic phases thereby both simplifying and making more cost effective overall purification and recovery process.

SUMMARY OF THE INVENTION

This invention is based, at least in part, on the surprising discovery that water can be effectively exchanged for an alcohol solvent. This allows for a process to recover an acid or salt thereof from an alcohol solvent without transitioning through the isolation of solids. Because of this, a process that is capable of providing a more economical operation and a more integrated continuous operation can be provided.

One example of a process according to the invention includes contacting an alcoholic phase containing one or more organic acid(s) or metal salt(s) thereof with water under conditions effective to provide an aqueous phase containing a portion of the organic acid(s) or metal salt(s) thereof. The aqueous phase does not contain substantial amounts of the alcohol(s). This process can also include recovery of the organic acid(s) or metal salt(s) thereof from the aqueous phase.

One specific embodiment of the invention relates to the use of this process in recovering ascorbic acid.

PREFERRED EMBODIMENTS OF THE INVENTION

The present invention relates, in one embodiment, to a process for recovering organic acids or metal salts thereof from an alcoholic phase. The processes can include contacting the alcoholic phase with water under conditions effective to provide an aqueous phase containing at least a portion of the organic acid(s) or metal salt(s) thereof and which aqueous phase does not contain substantial amounts of the alcohol.

This embodiment of the invention is capable of being employed in connection with any combination of organic acid(s) or metal salt(s) thereof with any alcohol so long as the organic acid/metal salt is at least partially soluble within the alcohol(s).

Specific examples of suitable organic acids include ascorbic, succinic, tartaric, gluconic, glyconic, citric, lactic, malic, maleic, acetic, formic, pyvuric, propionic, butyric, itaconic, gulonic and mixtures thereof. Moreover, the metal salts of these acids include any metal salts recognized the art such as alkali metal salts and alkaline earth metal salts with alkali metal salts being preferred. Specific examples of preferred metal salt include sodium salts.

As discussed above, any suitable alcoholic phase can be employed as long as the organic acid(s) or metal salt(s) thereof are at least partial soluble in the alcohol. The preferred alcoholic phase is depended on the particular acid being recovered.

One aspect of the inventive process involves contacting the alcoholic phase with water under conditions effective to provide an aqueous phase containing at least a portion of the organic acid(s) or metal salt(s) thereof. Preferably, the aqueous phase contains more than about 70% of the organic acid(s) or metal salt(s) thereof, with greater than about 85% being more preferred and greater than about 95% being even more preferred. In an embodiment of the invention, all, or at least substantially all, of the acid(s) and/or salt(s) are removed. By "substantially all" in this context, it is meant that only impurity level amounts would remain in the alcohol. Of course, the precise level of organic acid(s) and metal salt(s) removed is dependent upon the particular acid(s) and/or salt(s) being removed.

Moreover, this aqueous phase preferably does not contain substantial amounts of the alcohol(s). The ratio of water:alcohol(s) in the aqueous phase is preferably greater than about 50:50, more preferably about 70:30 to about 97:3, with about 90:10 to about 95:5 being even more preferred.

This contacting step may be accomplished in any reactor environment or apparatus suitable for vapor-liquid contacts specific examples of suitable apparatus include evaporator chambers and distillation columns with distillation columns being preferred in many environments.

The addition of water may be accomplished by, e.g. addition to either the liquid or vapor headspace within the apparatus. Moreover, the composition of the effluent from the chamber may be adjusted by the rate or the amount of water inlet stream to the rate of amount of the alcohol feed stream entering the apparatus or by simultaneously controlling the rate of alcohol overhead in the vapor space.

The process of the present invention can be effectively operated over a variety of operating conditions depending upon the particular process being employed. That is, the choice of temperature, pressure, time, etc., is dependent upon the particular alcohol/acid combination. Accordingly optimization of such parameters would be well within the purview of those skilled in the art.

In order to better illustrate the invention, this embodiment in the inventive process will now be discussed in terms of one specific example thereof, the separation of ascorbic acid from an alcoholic phase.

In this embodiment, solvent exchange of an alcoholic solution containing ascorbic acid or a metal ascorbate with water preferably occurs under conditions which allows removal of the alcohol in the vapor phase while maintaining the metal ascorbate soluble in the liquid phase. This process provides a means of transport or distribution of ascorbic acid or metal ascorbate from the alcohol to the water while simultaneously removing the alcohol from the mixture.

Figure 2:
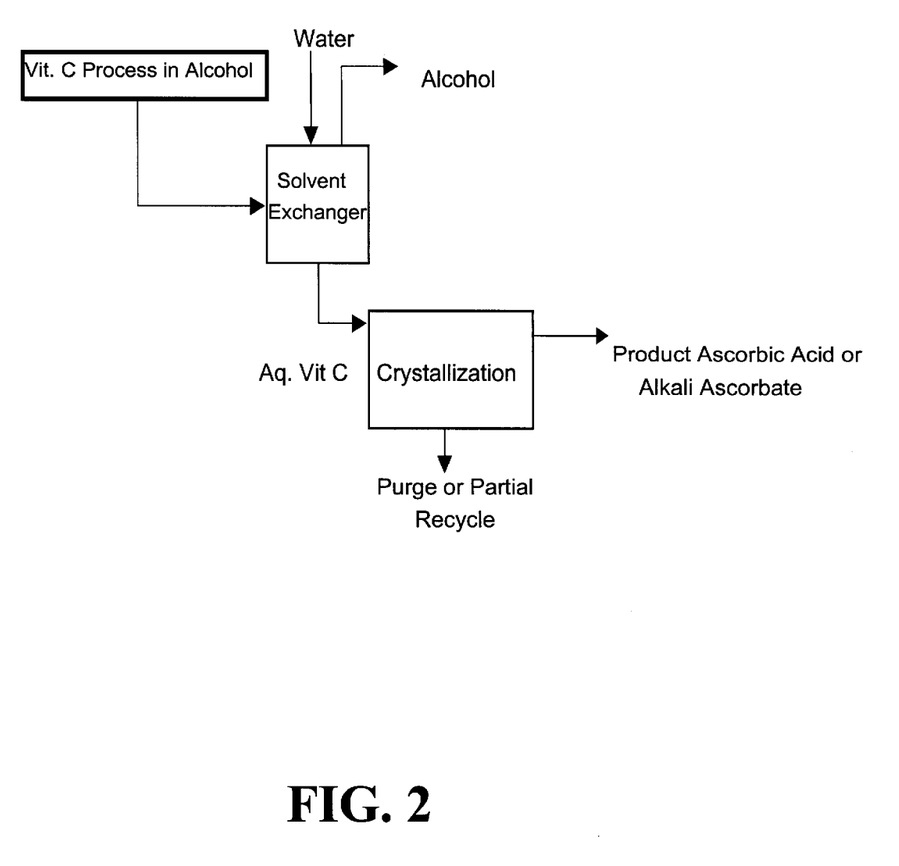
FIGS. 2–4 illustrate system according to the present invention for exchanging the alcoholic phase with an aqueous phase.

In a first system relating to this embodiment, as shown in FIG. 2, the ascorbic acid or metal ascorbate produced in an alcoholic solution may be fed to a solvent exchanger with water being co-fed to the system with removal of alcohol in the vapor phase. The liquid phase of the solvent exchanger can then be removed to produce an effluent containing ascorbic acid or metal ascorbate in an aqueous or water enriched alcoholic liquid phase containing the product. Isolation of the product can then be achieved by crystallization to obtain either ascorbic acid or alkali ascorbate.

Figure 3:
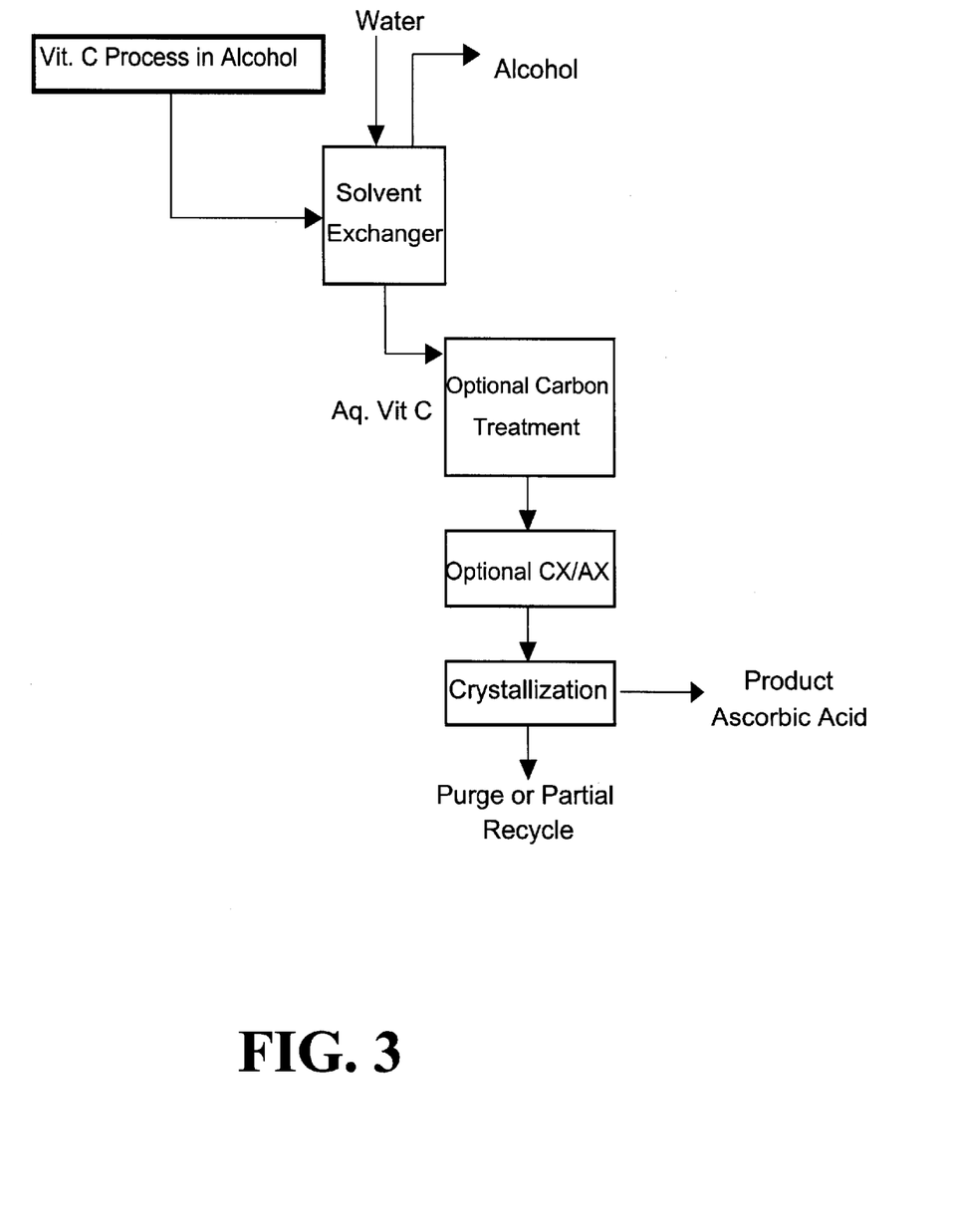

A second system relating to this embodiment is shown in FIG. 3 where ascorbic acid produced in an alcoholic solution may be fed to the solvent exchanger with the aqueous effluent optionally carbon treated for color removal, or ion exchanged by cation exchange and anion exchange to remove residual inorganics prior to the final crystallization step of ascorbic acid. These post-solvent exchanger steps may be operated independently or successively. These post-solvent exchanger treatments allow the process to be operated in a manner that allows greater product recovery and purity since the impurities will be removed from the stream being fed to the crystallizer.

Figure 4:
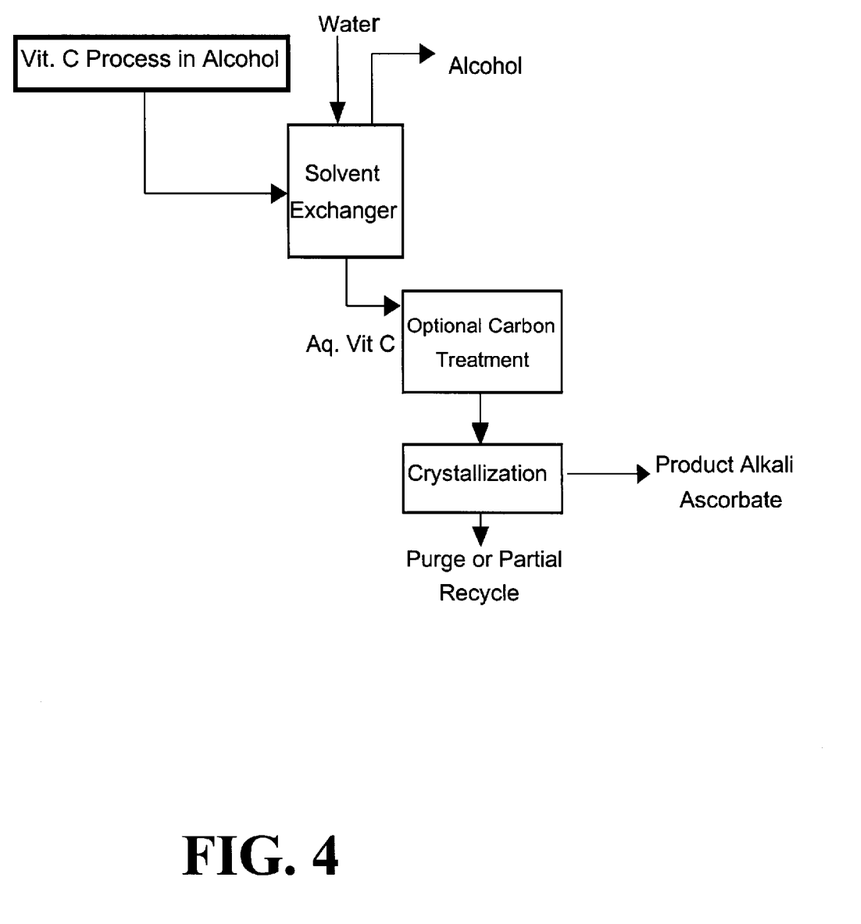

Alternatively, as shown in FIG. 4, metal ascorbate produced in an alcoholic solution may be fed to the solvent exchanger with the aqueous effluent optionally carbon treated for color removal prior to the final crystallization step of the alkali ascorbate. This post-solvent carbon treatment allows the process to be operated in a manner that allows greater product recovery and purity since the color bodies will be removed from the stream being fed to the crystallizer.

As discussed previously, this embodiment of the inventive process can be performed in any suitable apparatus, e.g., in an evaporative chamber, distillation apparatus or stripper, which allows removal of the alcohol in the vapor phase while maintaining the ascorbic acid or alkali ascorbate soluble in the liquid phase.

The solvent exchanger is preferably an evaporative chamber and, in particular, an evaporation chamber operated as a distillation column, with the base containing a liquid phase. The ascorbic acid or alkali ascorbate will accumulate in the liquid phase relative to the vapor phase that will partition most of the alcohol to be removed overhead from the system. A condenser may be employed to condense the alcohol, which may be reused or recycled as is or further purified by more extensive distillation.

The addition of water to the solvent exchanger may be achieved by either addition to the liquid or vapor headspace. Preferably, water vapor or steam would be added to provide the heat needed to vaporize the alcohol. The composition of the effluent of the exchanger may be adjusted by the rate or amount of water fed relative to the rate or amount of alcohol feed stream entering the solvent exchanger or by simultaneously controlling the rate of removal of the alcohol overhead in the vapor phase. By judicious control of these variables, the effluent composition or the liquid phase concentration may be adjusted accordingly. Preferably, the composition of the feed stream to the solvent exchanger would be maintained while the rate of feed of water and liquid removed from the base of the solvent exchanger may be adjusted to obtain a desired aqueous composition.

The effluent of the evaporative chamber or distillation column contains significantly reduced amount of alcohol relative to the feed stream and provides a more readily means of controlling the composition by adjustment of amount of alcohol removed from the system or the amount of water added to the system. The effluent from the exchange system containing the ascorbic acid or metal ascorbate in water, or mixture of alcoholic solution enriched with water, can then be processed in a manner that allows for direct isolation by crystallization, or subsequent purification treatment followed by crystallization.

Solvent exchange may be effectively preformed over a wide range of pressures with about 1 psia to about 20 psia being preferred. Solvent exchange may be performed over a wide range of temperatures with a preferred range of about 35° C. to about 80° C. Operation at about 50–70° C. and 8–17 psia can be particularly advantageous, especially with methanol as the alcohol being exchanged.

In this regard, a wide variety of alcohols can be employed, especially those that are miscible with water. In particular, alcohols having a wide range of chain length can be employed with chain lengths up to about butanol being more preferred. However, it can be advantageous to perform the esterification, lactonization, and solvent exchange with methanol as the alcohol. Methanol can be effectively employed in each step, and is especially easy to remove during solvent exchange due to its low boiling point that allows it to be easily removed in the vapor at atmospheric pressure.

The reasoning behind the preferred maximum $C_4$ chain length is to minimize the thermal degradation at temperatures above 80° C. Longer chain length alcohols not only require operation under reduced pressure to maintain a desired operating temperature, but also form azeotropes with water leading to a relatively impure alcohol vapor product.

The ascorbic acid or metal ascorbate fed to the exchanger may be produced by any technique recognized in the art.

Examples of suitable techniques include esterification of 2-keto-L-gulonic acid (KLG) with a mineral acid or strong acid resin in an alcoholic system to produce the corresponding ester, lactonization by treatment with an inorganic base or organic base to produce the alkali ascorbate, followed by specific steps to isolate either the alkali ascorbate or ascorbic acid.

Isolation of the intermediate ester by crystallization may be carried out, but is not required. For the production of the metal ascorbate, the crude lactonization stream can be fed directly to the solvent exchanger followed by the crystallizer. For the production of ascorbic acid, the lactonization stream may be protonated directly by acidification with mineral acid, such as sulfuric acid, removal of the insoluble acid salt by filtration followed by direct feed to the solvent exchanger. Further enhancement of the process for subsequent purification may be optionally carried out after the solvent exchanger. Or, the protonation may be carried out by ion exchange after the solvent exchanger.

Moreover, the KLG can be produced by any of a variety of techniques. For example, the KLG may originate from a fermentation process that involves the crystallization of 2-keto-L-gulonic acid from an aqueous broth or from the esterification of its corresponding salt in methanol. The KLG may also be produced from the hydrolysis of diaceton-2-keto-L-gulonic acid with a strong acid to deprotect the hydroxyl groups. However, the produced acetone by-product should be separated prior to the esterification step. Additionally, the use of KLG in its monhydrate form or its partial anhydride state may also be employed independent of the materials origin.

In other words, the process of the present invention is not dependent upon the technique employed to arrive at the alcoholic/acid phase. For example, in connection with the formation of KLG, any art recognized technique for forming KLG can employed. These techniques include both chemical processes such as the Reichstein processes, modified Reichstein process and the like as well as fermentation techniques. Once again, such techniques are well recognized in the art and need not be described in detail here.

As described above, the present invention provides an economical industrial process for efficiently producing ascorbic acid or a alkali ascorbate from an aqueous solution, produced initially from an alcoholic solution containing ascorbic acid or alkali ascorbate in such a way, that the handling of solids in the process of switching from methanol to water can be avoided. Moreover, a significant advantage of this process is the relative ease of handling the streams of liquids or slurries as opposed to handling of solids.

In particular, the process of the invention may be applied to a methanolic solution of ascorbic acid or sodium ascorbate produced by esterification of 2-keto-L-gulonic acid in methanol, followed by cyclization with sodium bicarbonate to produce a feed composition to the solvent exchanger to produce an aqueous product of ascorbic acid or sodium ascorbate. The product may then be obtained from the aqueous stream by crystallization.

The following examples further illustrate the present invention in detail but are not to be considered to limit the scope thereof.

EXAMPLES

Example 1

This example demonstrates the solvent exchange process operated with ascorbic acid in methanol as illustrated in FIG. 2. A solution of ascorbic acid was prepared by dissolving 50 g of Sigma ascorbic acid in 250 mL of methanol in a 500 mL 3-neck round bottom flask fitted with a condenser, graduated addition funnel, and a thermowell. The contents of the flask was stilled magnetically while being heated to reflux while maintaining a liquid temperature of 60° C. with aid of house vacuum applied to the condenser apparatus. Methanol vapor was removed overhead through the condenser and collected in a receiver. A total of 200 mL water was added while 200 mL of distillate was collected. The volume of the flask was reduced to about 100 mL and then cooled to about 15° C. to initiate crystallization. Crystals were collected by filtration and dried in a dessicator. The first crop weighed 27.2 g and had a purity of 100% by HPLC. The filtrate from the first crop was concentrated to about half the volume and cooled at 15° C. overnight. The crystals were collected by filtration and dried to give a second crop of 10.2 g and a purity of 100% by HPLC.

Example 2

This example demonstrates the solvent exchange process as illustrated in FIG. 3 originating from a sample of 2-keto-L-gulonic acid. A solution of 2-keto-L-gulonic acid was prepared by dissolving 50 g of 2-keto-L-gulonic acid in 250 mL of methanol in a 500 mL 3-neck round bottom flask fitted with a condenser, a cannulae tube, and a thermowell. A catalytic amount of sulfuric acid (1 g, concentrated H2SO4) was added and then the contents of the flask was heated to reflux (ca 65 C.) for 4 h under a nitrogen purge while being stirred magnetically. The reaction solution was allowed to cool to room temperature then 18.2 g of sodium bicarbonate suspended in 60 mL of methanol was added over 5 minutes via cannulae tube. The resulting suspension was heated to reflux with stirring for 3 h then cooled to room temperature. Sulfuric acid (12.0 g, concentrated H2SO4) was added slowly to a final pH of 3.3. The solution was heated to 50° C. then filtered through a Buchner funnel under nitrogen to remove the precipitated sodium sulfate.

The resulting solution of methanolic ascorbic acid was then fed to a solvent exchanger apparatus as follows: the above solution was placed in a 500 mL 3-neck round bottom flask fitted with a condenser, graduated addition funnel, and a thermowell. The contents of the flask was stirred magnetically while being heated to reflux while maintaining a liquid temperature of 50° C. with aid of house vacuum applied to the condenser apparatus. Methanol vapor was removed overhead through the condenser and collected in a receiver. A total of 200 mL water was added while 200 mL of distillate was collected.

The contents of the flask containing the ascorbic acid in aqueous methanol was carbon treated through a column of granular Darco activated carbon. The resulting solution was reduced to about 100 mL and then cooled to about 15° C. to initiate crystallization. Crystals were collected by filtration and dried in a dessicator. The first crop weighed 20.2 g and had a purity of 97% by HPLC. The filtrate from the first crop was concentrated to about half the volume and cooled at 15° C. for 4 h. The crystals were collected by filtration and dried to give a second crop of 1.8 g and a purity of 79% by HPLC. The filtrate from the second crop was concentrated to about half the volume and cooled at 15° C. for 4 h. The crystals were collected by filtration and dried to give a third crop of 2.8 g and a purity of 91% by HPLC.

Example 3

This example demonstrates the solvent exchange process as illustrated in FIG. 4 originating from a sample of methyl 2-keto-L-gulonate. A solution of methyl 2-keto-L-gulonate was prepared by dissolving 50 g of methyl 2-keto-L-gulonate in 250 mL of methanol in a 500 mL 3-neck round bottom flask fitted with a condenser, a cannulae tube, and a thermowell. A slurry of 19.8 g of sodium bicarbonate suspended in 60 mL of methanol was added over 5 minutes via cannulae tube. The resulting suspension was heated to reflux with stirring for 3 h then cooled to room temperature. The resulting slurry of methanolic sodium ascorbate was then fed to a solvent exchanger apparatus as follows: the above solution was placed in a 500 mL 3-neck round bottom flask fitted with a condenser, graduated addition funnel, and a thermowell. The contents of the flask was stirred magnetically while being heated to reflux while maintaining a liquid temperature of 50° C. with aid of house vacuum applied to the condenser apparatus. Methanol vapor was removed overhead through the condensor and collected in a receiver. A total of 200 mL water was added while 200 mL of distillate was collected.

The contents of the flask containing the sodium ascorbate in aqueous methanol was carbon treated through a column of granular Darco activated carbon. The resulting solution was treated with 150 mL methanol to precipitate the product. Crystals were collected by filtration and dried in a dessicator. The first crop weighed 3.8 g and had a purity of 93% by HPLC. The filtrate from the first crop was concentrated to about one third the volume and cooled at 15° C. for 4 h. The crystals were collected by filtration and dried to give a second crop of 25.1 g and a purity of 99% by HPLC.

Example 4

This example demonstrates the solvent exchange process as illustrated in FIG. 3 originating from a sample of methyl 2-keto-L-gulonate. A solution of methyl 2-keto-L-gulonate was prepared by dissolving 50 g of methyl 2-keto-L-gulonate in 250 mL of methanol in a 500 mL 3-neck round bottom flask fitted with a condenser, a cannulae tube, and a thermowell. A slurry of 19.8 g of sodium bicarbonate suspended in 60 mL of methanol was added over 5 minutes via cannulae tube. The resulting suspension was heated to reflux with stirring for 4 h then cooled to room temperature.

The resulting slurry of methanolic sodium ascorbate was then fed to a solvent exchanger apparatus as follows: the above solution was placed in a 500 mL 3-neck round bottom flask fitted with a condenser, graduated addition funnel, and a thermowell. The contents of the flask was stirred magnetically while being heated to reflux while maintaining a liquid temperature of 50° C. with aid of house vacuum applied to the condenser apparatus. Methanol vapor was removed overhead through the condenser and collected in a receiver. A total of 200 mL water was added while 200 mL of distillate was collected.

The contents of the flask containing the sodium ascorbate in aqueous methanol was passed through an ion exchange column of 160 mL of Ambersep 200 H resin. The column effluent was then treated with an anion exchange resin by adding 2.5 g of Amberlyte IRA 93 resin in a 500 mL round bottom flask with magnetic stirring for 2 h. The resin was removed by filtration and the aqueous ascorbic acid solution was then carbon treated through a column of granular Darco activated carbon. The resulting solution was reduced to about 100 mL and then cooled to about 15° C. to initiate crystallization. Crystals were collected by filtration and dried in a dessicator. The first crop weighed 19.5 g and had a purity of 96% by HPLC. The filtrate from the first crop was concentrated to about half the volume and cooled at 15° C. for 4 h. The crystals were collected by filtration and dried to give a second crop of 4.7 g and a purity of 100% by HPLC. The filtrate from the second crop was concentrated to about half the volume and cooled at 15 C. for 4 h. The crystals were collected by filtration and dried to give a third crop of 0.5 g and a purity of 100% by HPLC.

Example 5

This example demonstrates the solvent exchange process as illustrated in FIG. 3 originating from a sample of methyl 2-keto-L-gulonate. A solution of methyl 2-keto-L-gulonate was prepared by dissolving 50 g of methyl 2-keto-L-gulonate in 250 mL of methanol in a 500 mL 3-neck round bottom flask fitted with a condenser, a cannulae tube, and a thermowell. A slurry of 19.8 g of sodium bicarbonate suspended in 60 mL of methanol was added over 5 minutes via cannulae tube. The resulting suspension was heated to reflux with stirring for 4 h then cooled to room temperature. The resulting suspension was heated to reflux with stirring for 3 h then cooled to room temperature. Sulfuric acid (11.5 g, concentrated H2SO4) was added slowly to a final pH of 3.5. The solution was heated to 50° C. then filtered through a Buchner funnel under nitrogen to remove the precipitated sodium sulfate.

The resulting solution of methanolic ascorbic acid was then fed to a solvent exchanger apparatus as follows: the above solution was placed in a 500 mL 3-neck round bottom flask fitted with a condenser, graduated addition funnel, and a thermowell. The contents of the flask was stirred magnetically while being heated to reflux while maintaining a liquid temperature of 50° C. with aid of house vacuum applied to the condenser apparatus. Methanol vapor was removed overhead through the condenser and collected in a receiver. A total of 200 mL water was added while 200 mL of distillate was collected.

The contents of the flask containing the ascorbic acid in aqueous methanol was passed through an ion exchange column of 100 mL of Amberlyte 120H resin. The column effluent was then treated with an anion exchange resin by adding 2.5 g of Amberlyte IRA 93 resin in a 500 mL round bottom flask with magnetic stirring for 2 h. The resin was removed by filtration and the aqueous ascorbic acid solution was then carbon treated through a column of granular Darco activated carbon. The resulting solution was reduced to about 100 mL and then cooled to about 15° C. to initiate crystallization. Crystals were collected by filtration and dried in a dessicator. The first crop weighed 12.0 g and had a purity of 90% by HPLC. The filtrate from the first crop was concentrated to about half the volume and cooled at 15 C. for 4 h. The crystals were collected by filtration and dried to give a second crop of 9.8 g and a purity of 92% by HPLC.

Certain preferred and other embodiments of the present invention are discussed above. However, it is to be understood that various substitutions, modifications, omissions, and other changes are made without departing from the spirit thereof. Accordingly, the scope of the present invention is to be limited only by the scope of the following claims including equivalents thereof.

What is claimed is:

1. A process for recovering an organic acid or a metal salt from an alcoholic phase comprising:

(a) providing an alcoholic phase comprising (i) at least one organic acid selected from the group consisting of ascorbic and erythorbic acids and mixtures thereof or metal salt(s) thereof and (ii) at least one alcohol, wherein the organic acid or metal salt(s) thereof are at least partially soluble in the at least one alcohol;

(b) contacting the alcoholic phase with water under conditions effective to provide an aqueous phase containing at least a portion of the organic acid(s) or metal salt(s) thereof, which aqueous phase does not contain substantial amounts of the at least one alcohol, wherein the ratio of water: alcohol in the aqueous phase is from about 50:50 to 97:3 by weight; and (c) recovering at least a portion of the organic acid(s) or metal salt(s) thereof from the aqueous phase.

2. The process according to claim 1 wherein the at least one organic acid is ascorbic acid.

3. The process according to claim 1 wherein the metal salt is an alkali or alkaline earth metal salt.

4. The process according to claim 3 wherein the metal salt is an alkali metal salt.

5. The process according to claim 1 wherein the metal salt is an metal ascorbate.

6. The process according to claim 5 wherein the alkali metal ascorbate is produced from 2-keto-L-gulonic acid or diacetone-2-keto-L-gulonic acid(2,3;4,6-diisopropylidene-2-oxo-L-gulonic acid)monohydrate.

7. The process according to claim 6 wherein the 2-keto-L-gulonic acid is in its monohydrate form, or is partially converted to its anhydride form.

8. The process according to claim 6 wherein the 2-keto-L-gulonic acid is produced by a fermentation reaction.

9. The process according to claim 8 wherein the recovery step comprises crystallization of 2-keto-L-gulonic acid from an aqueous broth.

10. The process according to claim 6 wherein the 2-keto-L-gulonic acid is produced by the Reichstein process, protonation of a metallated salt of KLG, hydrolysis of diacetone-2-keto-L-gulonic acid(2,3;4,6-diisopropylidene-2-oxo-L-gulonic acid)monohydrate or hydrolysis of an ester.

11. The process according to claim 5 wherein step (a) comprises (i) esterifying 2-keto-L-gulonic acid and (ii) converting the 2-keto-L-gluonic acid ester to an ascorbate.

12. The process according to claim 11 wherein the esterification step (a) (i) occurs in the presence of strong acid selected from among sulfuric acid, hydrochloric acid and sulfonic acid.

13. The process according to claim 11 wherein the conversion step (a)(ii) is by way of an alkali metal base in an alcohol solution, wherein the alkali metal base is selected from among sodium carbonate, sodium bicarbonate, potassium carbonate, potassium bicarbonate, calcium carbonate, and sodium methylate.

14. The process according to claim 5 wherein the process further comprises, before step (b), protonating the ascorbate to maintain a pH of 1.5 to 3.5.

15. The process according to claim 14 wherein the protonation step comprises contacting the ascorbate with a strong acid selected such that metal salt(s) of the strong acid formed by protonation is only sparingly soluble in the alcoholic phase.

16. The process according to claim 15 wherein the strong acid is selected from the group consisting of sulfuric acid, hydrochloric acid and sulfonic acid.

17. The process according to claim 15 further comprising removing the metal salt(s) of the strong acid prior to step (b).

18. The process according to claim 17 wherein the metal salt is an alkali metal salt or an alkaline earth metal salt.

19. The process according to claim 17 wherein the step for removing the metal salt(s) comprises filtration, decantation, or centrifugation.

20. The process according to claim 5 wherein step (c) further comprises (i) contacting the aqueous phase with a sulfonic acid or cation exchange resin, (ii) contacting the product of step (i) with a weak anion exchange or tertiary amine resin and (iii) clarification of the resulting aqueous phase.

21. The process according to claim 1 wherein the at least one alcohol is selected from the group consisting of butanol, methanol, ethanol, propanol and mixtures thereof.

22. The process according to claim 1 wherein step (b) is performed at a temperature of 40–100 C.

23. The process according to claim 1 wherein step (b) is performed at a pressure of 1–20 psia.

24. The process according to claim 1 wherein step (b) comprises removal of the alcohol in the vapor phase.

25. The process according to claim 24 wherein step (b) is performed in an evaporative chamber or distillation apparatus.

26. The process according to claim 1 wherein step (c) comprises (i) contacting the aqueous phase with sulfonic acid or cation exchange resin.

27. The process according to claim 26 wherein step (c) further comprises contacting the product of step (i) with a weak anion exchange or tertiary amine resin.

28. The process according to claim 1 wherein step (c) comprises clarification of the aqueous phase.

29. The process according to claim 28 wherein clarification is performed with carbon.

30. The process according to claim 1 wherein step (c) comprises isolating the organic acid(s) or metal salt(s).

31. The process according to claim 30 wherein the isolating step comprises (i) crystallizing the acid(s) or metal salt(s) thereof from the aqueous solution, followed by (ii) at least one of filtration, decantation, centrifugation, and/or spray drying.

32. The process according to claim 1 wherein the organic acid is produced by way of a process that includes a fermentation step, the Reichstein process, protonation of a metallated intermediate compound, acidification of a salt of an intermediate acid, and/or hydrolysis of an ester.

33. The process according to claim 32 wherein the fermentation step is performed in the presence of at least one sugar related from glucose or sorbose.

34. A process for producing ascorbic acid or a metal ascorbate from 2-keto-L-gulonic acid or a metal salt thereof comprises:

a. esterification of 2-keto-L-gulonic acid or a metal salt thereof in a solvent comprising at least one alcohol:

b. converting the ester from step (a) to a metal ascorbate in the solvent;

c. exchange of at least a portion of the at least one alcohol solvent with water so as to provide aqueous metal ascorbate, wherein the ratio of water: alcohol is from 50:50 to 97:3 by weight.

35. A process for producing ascorbic acid or a metal ascorbate from 2-keto-L-gulonic acid or a metal salt thereof, comprises:

a. esterification of 2-keto-L-gulonic acid or a metal salt thereof in a solvent comprising at least one alcohol;

b. converting the ester from step (a) to a metal ascorbate in the solvent;

c. displacement of the ascorbic acid from the metal ascorbate;

d. exchange of at least a portion of the solvent of the at least one alcohol with water so as to provide aqueous ascorbic acid, wherein the ratio of water:alcohol is from 50:50 to 97:3 by weight; and e. separation of the ascorbic acid from the aqueous solvent.

36. The process according to claim 34 or 35 wherein the metal is an alkali metal or alkaline earth metal salt.

37. A process for producing ascorbic acid or an alkali metal ascorbate from 2-keto-L-gulonic acid or an alkali metal salt thereof, comprises:
   a. esterification of 2-keto-L-gulonic or an alkali metal salt thereof in a solvent comprising at least one alcohol;
   b. converting the ester from step (a) to provide an alkali metal ascorbate in the solvent;
   c. displacement of the ascorbic acid from the alkali metal ascorbate;
   d. exchange of at least a portion of the at least one alcohol solvent with water so as to provide aqueous ascorbic acid, wherein the ratio of water: alcohol is from 50:50 to 97:3; and
   e. separation of the ascorbic acid from the aqueous solvent.

38. The process according to any one of claims 34–37 wherein the 2-keto-L-gulonic acid is formed from fermentation.

* * * * *